(12) United States Patent
Klein et al.

(10) Patent No.: US 8,762,071 B2
(45) Date of Patent: *Jun. 24, 2014

(54) AUTOMATED SYSTEM FOR THE SELECTION AND CONVEYANCE OF STORED ALLOGENEIC BIOLOGICAL CELLS FOR TRANSPLANTATION, THERAPY AND RESEARCH

(75) Inventors: Thomas Klein, Potsdam (DE); Frank Keller, Berlin (DE)

(73) Assignee: Cytolon AG, Berlin (DE)

( * ) Notice: Subject to any disclaimer, the term of this patent is extended or adjusted under 35 U.S.C. 154(b) by 331 days.

This patent is subject to a terminal disclaimer.

(21) Appl. No.: 13/058,759

(22) PCT Filed: Aug. 14, 2009

(86) PCT No.: PCT/EP2009/006053
§ 371 (c)(1),
(2), (4) Date: Jul. 5, 2011

(87) PCT Pub. No.: WO2010/018002
PCT Pub. Date: Feb. 18, 2010

(65) Prior Publication Data
US 2011/0257999 A1    Oct. 20, 2011

Related U.S. Application Data

(60) Provisional application No. 61/090,079, filed on Aug. 19, 2008.

(30) Foreign Application Priority Data

Aug. 14, 2008    (EP) ..................................... 08075702

(51) Int. Cl.
G01N 33/48 (2006.01)
G06F 19/00 (2011.01)
G06Q 50/22 (2012.01)

(52) U.S. Cl.
CPC .......... *G06F 19/322* (2013.01); *G06F 19/3443* (2013.01); *G06Q 50/22* (2013.01)
USPC ......................................................... 702/19

(58) Field of Classification Search
CPC .... G06F 19/322; G06F 19/3443; G06Q 50/22
See application file for complete search history.

(56) References Cited

U.S. PATENT DOCUMENTS

| 6,707,561 | B1 | 3/2004 | Budach et al. |
| 8,498,882 | B2 | 7/2013 | Klein et al. |
| 2002/0132343 | A1 | 9/2002 | Lum |
| 2002/0168639 | A1 | 11/2002 | Muraca |
| 2003/0154108 | A1 | 8/2003 | Fletcher-Haynes et al. |
| 2004/0121369 | A1 | 6/2004 | Birkett et al. |
| 2005/0276792 | A1 | 12/2005 | Kaminski et al. |
| 2008/0014174 | A1 | 1/2008 | Kuroiwa et al. |
| 2008/0234945 | A1 | 9/2008 | Walk et al. |
| 2010/0248206 | A1* | 9/2010 | Kuypers et al. ................. 435/1.3 |
| 2011/0112864 | A1 | 5/2011 | Klein et al. |
| 2011/0257999 | A1 | 10/2011 | Klein et al. |
| 2012/0123792 | A1 | 5/2012 | Klein |
| 2013/0041680 | A1 | 2/2013 | Klein et al. |
| 2013/0132379 | A1 | 5/2013 | Klein et al. |

FOREIGN PATENT DOCUMENTS

| DE | 60030978 T2 | 6/2007 |
| GB | 2407193 | 4/2005 |
| WO | 02077640 A2 | 10/2002 |
| WO | 2005/097190 | 10/2005 |
| WO | 2007/070280 | 6/2007 |
| WO | 2010018002 A1 | 2/2010 |
| WO | 2010/089158 A1 | 8/2010 |
| WO | 2010/089159 A1 | 8/2010 |

OTHER PUBLICATIONS

Majhail et al., "Double umbilical cord blood transplantation," in Current Opinion in Immunology, vol. 18, No. 5, Oct. 1, 2006, pp. 571-575.
Informix, "Informix Guide to SQL—Tutorial—Informix Extended Parallel Server, Version 8.3 Informix—Dynamic Server 2000, Version 9.2," Dec. 31, 1999. Internet Citation, Retrieved from the Internet: URL: http://publib.boulder.ibm.com/epubs/pdf/6530.pdf>.
Anonymous: "Cord blood forum: Annotated Bibliography-Cell Dose" in Internet Citation, Jan. 20, 2008, Retrieved from the Internet: URL: http://web.archive.org/web/20080120203934 / http://cordbloodforum.org/biblio/v_donorselect/index.html (Best Copy).
Anonymous: "Cord Blood Forum: annotated Bibliography—Multi-Cord Transplants" in Internet Citation May 10, 2008, Retrieved from the Internet: URL: http://web.archive.org/web/20080510110817 / http://www.cordbloodforum.org/biblio/iii_multicord/index.html.
Office Action of Jun. 21, 2012 issued in U.S. Appl. No. 12/934,578 (Jun. 21, 2012).
Lee SJ, Kamani N, Confer DL, Principles and tools for selection of umbilical cord blood and unrelated adult donor grafts, Biol Blood Marrow Transplant. Jan. 2008;14(1 Suppl 1 ):112-9.

(Continued)

*Primary Examiner* — Anna Skibinsky
(74) *Attorney, Agent, or Firm* — Joyce von Natzmer; Agris & von Natzmer LLP

(57) ABSTRACT

The invention relates to a system for the automatic, rapid and dynamic conveyance of biological cells for transplant, therapy or research purposes between withdrawal centres or banks (storage facilities) and clinics, transplant centres or research facilities and also for the monitaring and backing of the processes from request transmission, for supply of a cell specimen which is suitable for the allogeneic transplant, through application of the conveyed specimens to tracking of the results in a patient and the provision of these data for statistical and other purposes. For the first time, the system is able to put forward complete solution proposals for specifically stored transplants online and automatically.

5 Claims, 3 Drawing Sheets

(56) References Cited

OTHER PUBLICATIONS

Figure 1:
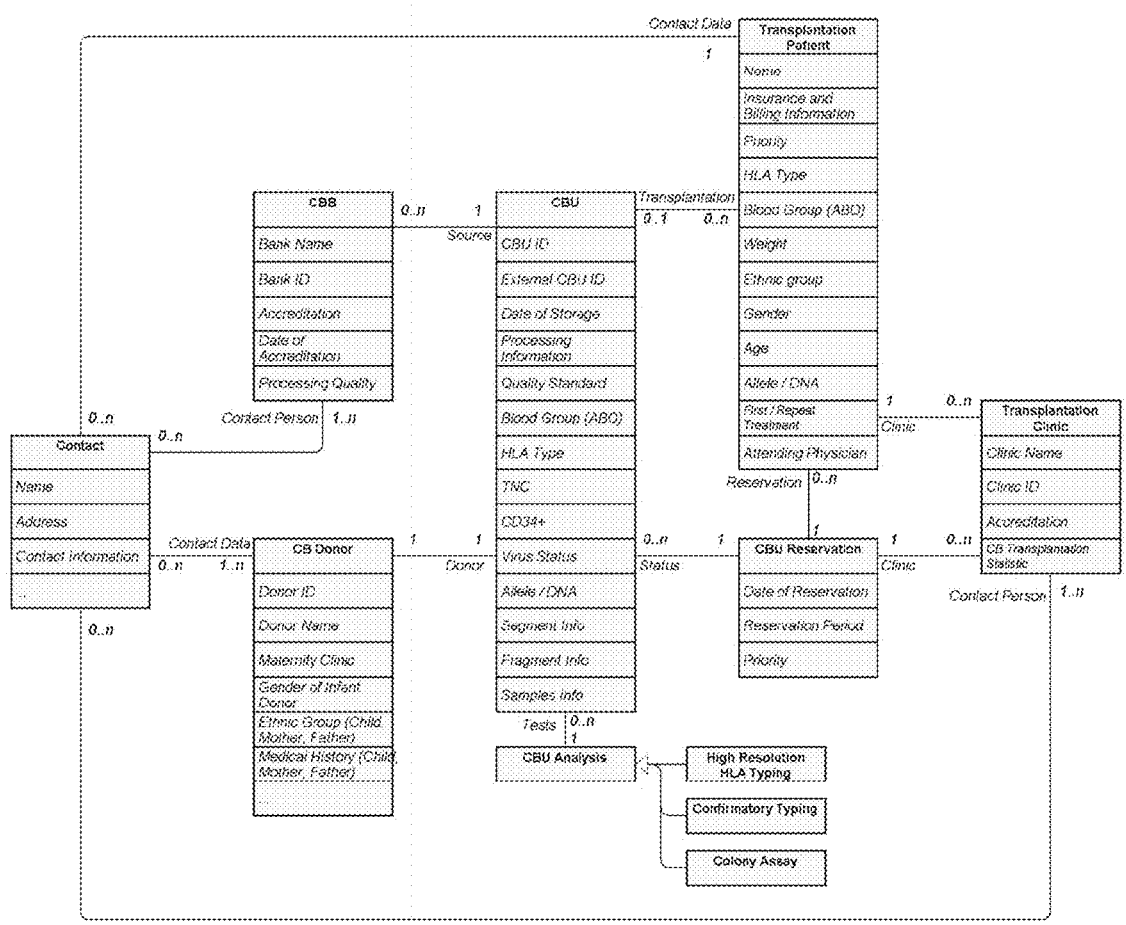

Wall DA, Chan KW, Selection of cord blood unit(s) for transplantation, Bone Marrow Transplant. Jul. 2008;42(1):1-7.
Petersdorf EW, Optimal HLA matching in hematopoietic cell transplantation, Cur Opin Immunol. Oct. 2008;20 (5):588-93.
Gluckman E, Rocha V, Donor selection for unrelated cord blood transplants, Curr Opin Immunol. Oct. 2006;18 (5):565-70.
Notice of Allowance issued in U.S. Appl. No. 13/147,835 on Apr. 16, 2013.
Hurley C K et al: "Hematopoietic stem cell donor registry strategies for assigning search determinants and matching relationships.", in: Bone Marrow Transplantation Feb. 2004 LNKD-PUBMED:14676778, vol. 33, No. 4, 2004-02, pp. 443-450.
Office Action issued in U.S. Appl. No. 12/934,578 on Jun. 21, 2012.
Mathematical Symbols, RapidTables.com: Online Reference & Tools, accessed on Jan. 17, 2014 at http://www.rapidtables.com/math/symbols/Basic_Math_Symbols.htm.
U.S. Appl. No. 13/953,555, filed Jul. 29, 2013.

* cited by examiner

AUTOMATED SYSTEM FOR THE SELECTION AND CONVEYANCE OF STORED ALLOGENEIC BIOLOGICAL CELLS FOR TRANSPLANTATION, THERAPY AND RESEARCH

This is the U.S. national stage of International application PCT/EP2009/006053, filed Aug. 14, 2009 designating the United States which claims priority to European Application EP 08075702.4, filed Aug. 14, 2008 and the benefit of U.S. provisional application 61/090,079, filed Aug. 19, 2008.

The invention relates to a system for the automated, quick and dynamic transmission of biological cells for transplantation, therapy or research purposes between collection centers or banks (storage locations) and clinics, transplantation centers or research institutes as well as monitoring and support of the processes from submitting a request to the delivery of a cell product which is suitable for allogeneic transplantation, ranging from the use of the products sent to follow-up on the results in the patients and the provision of these data for statistical and other purposes. For the first time, the system can propose online and automatic complete solution suggestions for specifically stored transplantations.

In recent years, various processes and methods have developed for provision of umbilical cord blood- (UCB-) preparations between collection centers or umbilical cord blood banks on the one hand, and clinics or transplantation centers on the other hand. All processes and methods are based on the processes required for procuration of bone marrow. Thus far, there are no automated processes. A clinic which requires a UCB-preparation for transplantation for a patient/recipient inquires with registries whether they have a UCB-preparation for their patient which is a match according to various biological and medical identification factors. The registered data refer to the so called HLA match, the cell count in the preparation, and other medical/biological data (such as the blood group).

Clinics and transplantation centers have so called coordinators who select a UCB-transplant using the transmitted data. These coordinators recommend a selection of preparations to the treating physician. The physician decides whether and which transplant will be used. In order to allow the clinics to order the correct umbilical cord blood unit, the clinic must inquire about all significant data regarding the preparation for each respective preparation.

However no worldwide standards have been defined thus far for the information which is filed in a so called Unit Report. Furthermore the correlation of the data of individual preparations in relation to each other has not been covered thus far. When selecting preparations, coordinators are subject to an iterative process which is time-consuming and susceptible to errors.

This problem is further intensified by the fact that many stored UCB-preparations which would be suitable e.g. according to the HLA match, are too small for transplantation; that is, the cell count of the preparation is too low. Clinical research over the past five years has proven that the number of nucleus containing cells (TC) contained in umbilical cord blood, and subordinate to this, the so called CD34+ cells (which have the ability to form blood) are of decisive significance for the success of the transplantation. The precision of the genetic fit (HLA match) can be much lower in a large cell count than, for instance, the required HLA match in bone marrow transplants. The required cell counts and their correlation with the HLA match are described in the state of the art, but have not yet become a systematic part of the established procedures. Today, coordinators and cord banks are faced with the task of identifying matching preparations in individual tests and comparing them to the patient data. This is all the more difficult since the possibly suitable preparations are usually located in several banks and described using different processes and standards.

The state of the art, such as US 2002/0132343 A1, discloses that the successful treatment of (leukemia, etc.) patients with suitable umbilical cord blood preparations requires a high cell count and a high/guaranteed level of product quality (incl. FDA, etc. certification), and that they can also be provided for simple and direct use in the transplantation clinic. A comprehensive system (SCBS) is described for expanded and matched stem cells (not only umbilical cord blood), comprising the entire life and production cycle (source material collection, production, certified quality assurance and delivery). The comprehensive system fulfils the regulatory quality requirements and standards according to the FDA, such as: FACT, CGTP, AAB and a preparation which matches the patient's tissues is selected from an existing (allogeneic) umbilical cord blood supply (matching). US 2002/0132343 A1 describes that the known methods for typing (HLA typing of at least six loci) of the donor and patient cells must be used, in compliance with the regulatory standards. It is also described that an automated tracking system can be used to track the individual preparations/samples and for follow-up. The donor cells (source material) originate from a certified source (umbilical cord blood bank) which records the relevant information (e.g. TNC, HLA loci, numbers of CD34+ cells) for each sample according to the quality standards. According to US 2002/0132343 A1, the source material is processed so that only the relevant cells are further processed, and the desired cells (such as CD34+ cells) are expanded ex vivo. The stem cell products which are produced in this manner are made ready for use as a "Patient Treatment Kit". They have defined characteristics and can be directly used by the treating physician. An ordered SCBS product matches at least 4/6 antigens or 3/6 alleles with $2*10^7$ cells/kg in children (<12Y) or patients with <50 kg body weight as well as $1*10^7$ cells/kg bodyweight in all other patients. US 2002/0132343 A1 describes a central element in terms of the ability to deliver the SOBS products directly to the transplantation centers which have ordered the product. For this purpose, the SOBS products are packaged into special containers which are shipped using courier services. Quality standards are maintained in this process. The described SOBS system and the methods do not take the problems of the automated selection of suitable products into account. The current state of the art for manual selection of stem cell products is described (HLA matching, cell count/weight correlation, etc.). US 2002/0132343 A1 does not show how the required time for identifying suitable donor material can be reduced or how the required manual steps for selecting between several potentially suitable products could be automated.

US 2002/0168639 A1 also discloses that due to the limited performance capacity of the analysis devices, it is difficult to compare a tissue sample to a large number of comparison samples. US 2002/0168639 A1 describes a profile carrier on which a tissue sample can be housed and which also comprises a micro-array on which different comparison samples can be used for analysis. The reaction capacity of the test tissues or the micro-array samples is saved in a database and placed in relation to other information regarding the patient from whom the test tissues originate (e.g. age, weight, sex, medical history). The database system disclosed in US 2002/0168639 A1 is linked to an Information Management System (IMS) which can perform searches and correlations. It generates comparisons and correlations of the biological reaction capacities between the test tissues and the samples of the micro-array. The abilities of state of the art business analysis products to perform data analysis and visualization, as in "Tibco Spotfire", are applied here. Within the scope of US 2002/0168639 A1, information about tissue cells and their donors is collected and saved. This information is compared using standard analysis procedures in order to identify correlations etc. for research and diagnostic purposes. It is not disclosed how the correlation would take place in relation to a concrete enquiry. Instead, reference is made to the general options which correspond to the state of the art.

GB 2407193 A describes a system for having biological cell line experiments with image evaluation take place and be evaluated in an automated process. On the one hand, the system consists of a unit which makes it possible to define new experiments and have them take place in an automated process, wherein the system is open in that any desired experiments and devices can be registered and used in a modular manner. The second system component covers the automated analysis (image referencing) of the experiments—herein, referencing is performed primarily to the image evaluation of assays; that is, the results of the assays (the experiments) are entered into the system and analyzed by it. Variable/expandable analysis techniques can be used. The entire system independently controls the implementation and analysis of several subsequent experiments. The implementation process can be flexibly defined/adjusted for this purpose. The results are saved in a database, and the results are shown to the user using flexibly definable reports. GB 2407193 A shows that entire laboratory processes for experiments with cell lines can be automated. Something similar is known from the industrial practices of numerous application domains. GB 2407193 A provides a general structure for automated data evaluation within the scope of the process.

US 2004/0121369 A1 addresses the problem of automating the flexible use of numerous devices and analysis methods within the scope of complex biological laboratory experiments. Sending data through consecutive differing software applications within changing laboratory processes or processing data in parallel is time consuming and requires individual human coordination (manual data formatting or time-consuming individual programming). US 2004/0121369 A1 provides a flexible framework for the automation of laboratory experiments and their evaluation. The system enables flexible registration (connection) of laboratory device controls to use them in individually and freely definable experiment processes. Analysis devices and analysis software can also be flexibly registered and integrated into the overall process. For this purpose, US 2004/0121369 A1 describes a flexible registration mechanism which solves the problem of different interfaces and protocols of devices and analysis applications so that they can be linked together efficiently. The information is saved in a database. US 2004/0121369 A1 addresses the problem of increasing efficiency in specific processes. It is shown that tasks which formerly required manual support by trained personnel can run fully automated. However the solution of the problem lies within the field of efficient device connection, and not in the field of efficient selection of specific cell products.

WO 02/077640 A2 discloses a system for efficiently processing and evaluating large amounts of data which are formed when analyzing biomolecules using micro-arrays, and optimizing the analysis process in this manner. The disclosed automated system makes it possible to group large amounts of data in a database using data mining processes, e.g. by physical attributes, and analyzing these results with a self-learning neuronal network. Using mathematical and statistical methods, the neuronal network makes it possible to automatically generate new samples which fulfill a desired task. Consequently mathematical and statistical (self-learning) algorithms are used to answer specific questions regarding a sought biomolecule. However the algorithms are not transferable into other systems, but can only be used within the stated system.

US 2008/0014174 A1 describes the methodical production of lymphocyte products as well as their storage and a kit for ready use in patients. The lymphocytes originate from the peripheral blood of donors which match the patient in at least 4 loci. Specific tumors, viral infections and autoimmune disorders are to be treated with HLA matched allogeneic activated lymphocytes. No statements are made regarding the precise selection process.

DE 600 30 978 T2 furthermore discloses a process which makes it possible to simultaneously analyze several biological samples quantitatively in a high-quality manner using a sensor platform. In particular, the chemical and physical attributes of a sample that is being analyzed are determined by the sensor platform and sent to a signal evaluation process. Among other things, the system can be used to determine the HLA parameters of samples.

The state of the art does not describe precisely how the products are selected. It is generally known which parameters should be used to select suitable products, but it cannot be determined how the "best" product can be selected from among the analyzed products. The state of the art furthermore does not describe a selection system which describes a suitable product and presents the results to the coordinator, and which can run automatically.

Furthermore, no documents mention the problem of multiple transplantation. This is a solution strategy if no suitably sized product is found. The search is then expanded to two or more products which contain sufficient cells together and also have a sufficient HLA match both with each other and with the patient. This problem can also be solved automatically with this invention.

The task of the invention accordingly comprises providing a system which does not possess the disadvantages of the state of the art, and allows the selection and distribution of a suitable product.

Surprisingly, the task is solved by the independent claims. Preferred embodiments of the invention are shown in the sub-claims.

It was completely surprising that a system for the provision and selection of biological cells or tissues, particularly umbilical cord blood preparations, for transplantations, therapy and/or research purposes between at least one collection centre and/or a storage location and at least one clinic, a transplantation centre and/or a research institute, wherein the system comprises the following steps:

Data processing,
Presetting of search criteria,
Patient search and/or
Order processing and tracking, wherein
the potential umbilical cord blood preparations in particular are arranged and selected according to an HLA match, patient weight, number of nucleus containing cells (TNC) and number of haematopoietic cells (CD34+) does not have the disadvantages of the state of the art.

In the sense of the invention, a system describes an entirety of individual components which are related to each other and interact. Advantageously, a system may comprise both programs and DP systems (data processing systems) as well as physical elements such as transport containers and UCB-preparations.

The teaching according to the invention is also a combination invention wherein the stated elements interact in order to attain an overall technical success and a synergistic effect is produced, which is shown in the surprising attributes of the system. The system according to the invention compares the incoming patient data to the data of registered cell preparations using a multi-level compatibility matrix and varying classification criteria. The comparison is preferably fully automatic, wherein a treating physician will preferably have online access to the data. The physician may preferably be provided automatically with recommended solutions regarding the individual preparation (single transplant) or matching preparations (multi-transplant) which would be suitable for transplantation. This fundamentally changes and significantly improves the actual benefit of the "ready-to-use" UCB-preparations as compared to the lengthy comparative search done by coordinators. The system is suitable for all biological, biochemical or chemical substances which are subject to time critical transmission for transplantations or other (medical) applications.

Herein information about the patient and the preparation (e.g. HLA parameters or weight and cell count) is preferably correlated by information processing systems and used to evaluate compatibilities. The information about available umbilical cord blood preparations (UCBP) is preferably provided and updated de-centrally by the blood banks. The information about the available UCBP inventory can, for instance, be combined in a repository (database) where it is provided for searches. In order to increase efficiency and reduce errors, the search parameters used for the weighting and automated selection can, for instance, be centrally stored for the treating physicians and clinics. At the start of a search, the pre-set search parameter sets can be brought up and modified by an expert if required (expert mode). A search for matching UCBP will preferably take place automatically, but can also be performed or verified step by step by a professional. Preparations for order processing may require interactions with the blood bank to initiate further or missing tests. Thus far, this is a manual and time-consuming step. The system preferably supports the processes with an automated work flow; that is, a work flow which takes place in a predefined series of activities within an organization. The work flow constantly provides information about the upcoming orders and the work status of individual orders, which improves the quality of the results and ensures that the processes in themselves take place more rapidly and efficiently. In the follow-up regarding the delivered and transplanted preparations, the system is able to compile the medically and pharmacologically required information. In a preferred embodiment, the system is also automatically able to generate statistics regarding the processing speed and speed of the blood banks as well as success statistics depending on illness types and UCBP-parameters. This provides the system user, such as the coordinator, with a clear overview of the processes he can use to improve work processes or order processing, since it provides him with valuable evaluations e.g. regarding the blood bank.

It is preferable that during data processing, all UCB-preparations which are stored in various UCB-banks or collection centers worldwide are particularly recorded using a preferably uniform data set (Unit Report) as parameters. The parameters comprise:
    name and identification of storing UCB bank
    status of depositing UCB bank with regard to international certifications (e.g. FACT)
    process reliability of the UCB bank according to classification
    contact in the respective bank, including contact data
    identification number of preparation
    medical history of mother, child and family according to the anamnesis sheet from the maternity clinic
    ethnic group of mother, father and/or child
    sex of child
    date of initial storage of preparation
    details of preparation processing
    blood group of preparation
    HLA type of preparation
    cell count (TNC) of preparation
    cell count (CD34+) of preparation
    viral status of preparation
    allelic characteristics of preparation The combined parameters are preferably entered into the system and surprisingly enable a unique description of a umbilical cord blood preparation (UCBP), since each preparation is defined by its specific attributes or parameters on the basis of the entered data and/or the combination of the parameters. This is preferably attained by combined recording of the parameters. In the sense of the invention, a parameter describes a key figure, that is, a characterizing attribute, which are entered into the system as data. They preferably comprise operational information (attributes) of patients, clinics, physicians, donors, blood banks, UCB-preparations (laboratory parameters, physical and informational attributes), order and processing information and controlling information e.g. search and exclusion criteria, threshold parameters and weighting factors.

Parameters which are used to identify the preparations are used herein. In particular, the beneficial combination of parameters is not described in the state of the art, and allows a unique allocation and recordation of a preparation. In this manner, it is possible to create a Database, a UCBP Database in the sense of the invention, in which the parameters are saved. A particularly preferable aspect of the application is shown as an example in FIG. 1.

The parameters can be entered e.g. de-centrally by the UCB-bank, which can also maintain and update the database, respectively. Aside from the information from the umbilical cord blood bank (UCB-bank), such as the name and identification of the UCB-bank, the status of the bank regarding international certification (e.g. Fact—"Foundation for the Accreditation of Cellular Therapy") is also saved, which makes it possible to ensure compliance with defined standards regarding the quality of the preparations. A contact person at the respective bank with contact data can also be advantageously entered. Here the contact person may be e.g. a treating physician or a coordinator who is responsible for database maintenance at the bank. Furthermore an identification number which is uniform within the system (ID) is preferably assigned to allow unique allocation. This also enables searches for preparations of the UCB-bank and overlapping. Furthermore, processing reliability information for each UCB-bank is automatically collected by the system and taken into account in the search. Furthermore, data on the medical history of the mother, child and family are also comprised in the database according to a history sheet from the birth clinic. This allows the beneficial assessment of the preparations regarding specific illnesses, such as inherited disorders. The ethnicity of the mother, father and/or child is beneficial as information since certain genetic variations may be associated with the ethnic background and may therefore complicate transplantation. Furthermore, parameters such as the blood group, HLA type, cell count (TNC="total nuclear cells" and CD34+), the viral status and allele form of the preparations are preferably entered into the database. This extensive information enables characterization and identification of the preparations and accordingly, optimal allocation of a recipient.

The data set of each preparation preferably contains information about whether the preparation was frozen in segments (if yes, how many) and with fragments (if yes, how many) and DNA samples (if yes, how many). Fragments, segments and samples are used for the later closer identification of the sample regarding a specific patient and to verify central data prior to transplantation. The system provides information about how many of the segments, fragments and DNA samples are currently still available at the time of the enquiry, or what further tests such as CT (Confirmatory Typing), HR (High-Resolution HLA-Typing) or CA (Colony Assays) were already done and what the results of these tests were. The status of a preparation is also recorded; that is, whether and since when the preparation may have been reserved by a clinic.

In the sense of the invention, the database, including the data or parameters, can also be comprehensively referred to as a data warehouse whose content is comprised of data from differing sources. It not only manages all data of the individual preparations in the different UCB-banks, but also dynamically matches all preparations which are entered against all other preparations in the various UCB-banks, so that it is automatically documented with the registration of each preparation which preparations can be used together later for a possible double or multiple transplantation (MultiCord).

The first order criterion for this multi-cord comparison between registered preparations is the HLA match. There is mainly agreement in at least four out of six HLA attributes. In the order of suitability as multi-cords, the preparations which have the greatest number of HLA matches are at the top. Preparations which have e.g. a negative viral status, that is, they are proven not to contain a specific virus, are not taken into account. In the sense of the invention, an order describes a defined series of elements. The order of the elements may refer to their attributes, such as the parameters or attributes (e.g. UCB-preparations). In the sense of the invention, the classification criteria describe how the order comes into existence (e.g. all UCB-preparations are sorted by their TNC figure from the largest to the smallest preparation). It is advantageously possible to apply filter criteria to an classification; that is, it is possible to e.g. take only preparations into account for a search which possess a defined TNC size. It is particularly beneficial that these classifications can be used in greater data quantities e.g. to perform efficient searches (also as a combination which covers several criteria).

The second order criterion is blood group matching or compatibility. Preparations with blood group matches are again at the top; those which are compatible follow; and blood groups which exclude each other lead to unsuitability as multi-cords of specific other preparations.

The cell count (TNC and CD34+), ethnicity and allele form are comprised as information or attributes of the preparations and serve to determine the further order; that is, whether the preparations would be suitable, or whether it would be beneficial to verify another attribute of the preparations. Preparations with a high TNC cell count and a high CD34+ cell count are again at the top. The same applies to identical ethnic origins and compatible allele forms. Therefore possible pairs or groups of compatible preparations are already identified and placed in order of priority in the system database; that is, the data within the system, before inquiries by a clinic for an individual patient.

The requesting clinic preferably performs patient research, wherein the determining comprises patient-compatible preparations according to the following classification and/or exclusion criteria:

name and identification of clinic or transplantation center
names of coordinator and attending physician, including contact data
status of clinic with regard to international certifications (e.g. Fact)
average number of UCB transplantations in the inquiring clinic during the last three years
name of patient, insurance number and other accounting information
patient's medical history
indication and therapy proposal of attending physician
urgency according to defined classification
HLA type of patient
blood group of patient
weight of patient
ethnic group of patient
sex of patient
age of patient
known allelic characteristics of patient and/or data of DNA typing, and/or
first treatment or re-treatment.

The beneficial combination of the order and/or exclusion criteria which work together synergistically makes it possible to uniquely characterize a patient, wherein the data of a patient are advantageously compared to the saved data of a preparation in a UCB-bank. The patient and preparation are preferably characterized using the same criteria, allowing a direct comparison. Herein the attributes of the preparations can be advantageously compared to those of a patient, e.g. using a compatibility matrix, in several levels and with various classification criteria. The compatibility matrix allows a direct and simple comparison of the attributes of the preparations with those of the patient and provides information about whether the preparation is compatible for the patient. The treating physician is preferably presented with several results, that is preparations, which would be optimal for a patient. Furthermore preparations for single cords or multi cords can preferably be recommended with regard to transplantation in a specific patient. The final decision as to which preparation(s) is/are used can preferably be made by the treating physician. FIG. 1 shows a particularly preferred embodiment of the embodiment.

In the sense of the invention, the criterion Indication and therapy recommendation of the treating physician describes the diagnosis, analysis and indication of the illness from which the patient suffers (such as Acute Myeloid Leukemia (AML) or Ischaemic Stroke) and for which the treating physician recommends a specific treatment (therapy). The therapy recommendation comprises, among other things, a specification of the preparation to be used (such as a umbilical cord blood preparation as a ready-made medicinal preparation), the time, progression and duration of the treatment as well as the number, dosage and administration of the preparation(s) and possible measures in case of relapse.

Furthermore, in the sense of the invention, the criterion urgency according to defined classification describes the priority of the search and allocation of a suitable preparation for a specific patient which is bindingly specified for all users of the database or platform as compared to a parallel search for another patient, both of whom may be suitable for the same preparation in the inventory on the basis of the genetic typing.

The classification table may be specified by a coordinator and is oriented to the medical urgency with which the patient requires the preparation.

The parameters which may e.g. be important for a specific patient and which are consequently important in the search for a suitable preparation may be advantageously predefined by a treating physician or the clinic prior to the search, which enables an efficient and automated search process.

For instance, the information about the treating clinic is not only recorded for the quality assurance of the process, but also collected in advance as required information without which the search process cannot start. The preferred embodiment furthermore automatically collects statistical information about each clinic regarding the number and type of transplantations, which simplifies the assessment of a clinic regarding its suitability for transplantation. This makes it particularly simple to exclude clinics which have little or no experience with transplantations.

The urgency of the case, e.g. the transplantation, is taken into account when prioritizing preparations in case of conflicts. It is beneficial for process automation if potentially occurring conflicts regarding reservation and ordering of UCB-preparations can be solved. Among other things, the prioritization information can be used for this purpose. Furthermore, it is also beneficial to collect information required for automated billing. This is a mandatory prerequisite particularly in automated mass processing, significantly simplifying the automation, and therefore constituting a significant reduction of work steps.

During the preferred automatic selection of a suitable preparation, it is preferably possible to call up information or lists of the suitable preparations at any level. This provides a clear overview of the selection for the coordinator or expert person implementing the search.

The order of potential umbilical cord blood preparations is preferably specified as follows:

$ML_{Prep}$=match level according to HLA compatibility between preparation and patient $$ML_{Prep} := \begin{cases} 6: HLA_{Prep} \text{ und } HLA_{Pat} \text{ match in 6 of 6 values and blood group compatibility} \\ 5: HLA_{Prep} \text{ und } HLA_{Pat} \text{ match in 5 of 6 values and blood group compatibility} \\ 4: HLA_{Prep} \text{ und } HLA_{Pat} \text{ match in 4 of 6 values and blood group compatibility} \\ \text{preparation not included: other} \end{cases}$$

$CF_{prep}$=cell factor defines the required number of cells per kg of patient weight at corresponding match level $$CF_{Prep} := \begin{cases} 3 \times 10^7: ML_{Prep} = 6 \\ 4 \times 10^7: ML_{Prep} = 5 \\ 5 \times 10^7: ML_{Prep} = 4 \end{cases}$$

$CN_{Prep}$=classification number of a preparation allowing arrangement of preparations according to TNC and match level $$CN_{Prep} := \frac{TNC_{Prep}}{CF_{Prep}}$$

$SL_{Single}$=short list of preparations to be considered for single transplants $$SL_{Single} := \left\{ p \in Prep \,\middle|\, \frac{CN_p}{BW_{Pat}} \geq 1/kg \wedge ML_{Prep} \geq 4 \right\}$$

The standard classifications of the preparations in a shortlist are set by the following criteria:

Classification 1=initial ranking according to match level, followed by classification number, followed by DC34+

$$\text{Classification 1 } (SL) := \left\{ p1 \in SL, \right.$$
$$p2 \in SL \left| \begin{array}{l} \text{either } ML_{p1} > ML_{p2} \\ \text{or } ML_{p1} = ML_{p2} \wedge CN_{p1} > CN_{p2} \\ \text{or } ML_{p1} = ML_{p2} \wedge CN_{p1} = CN_{p2} \wedge CD34_{p1} \geq CD34_{p2} \end{array} \right\}$$

Classification 2=initial ranking according to match level, followed by classification number, followed by DC34+

$$\text{Classification 2 } (SL) := \left\{ p1 \in SL, \right.$$
$$p2 \in SL \left| \begin{array}{l} \text{either } CN_{p1} > CN_{p2} \\ \text{or } CN_{p1} = CN_{p2} \wedge ML_{p1} > ML_{p2} \\ \text{or } CN_{p1} = CN_{p2} \wedge ML_{p1} = ML_{p2} \wedge CD34_{p1}^+ \geq CD34_{p2}^+ \end{array} \right\}$$

Herein the following corresponds:
Prep=umbilical cord blood preparation
Pat=patient
$HLA_{Prep}$=HLA parameters of the patient
$HLA_{Prod}$=HLA parameters of a preparation
$TNC_{Prep}$=number of nucleated cells of preparation
$BW_{Pat}$=body weight of patient in kg
$CD34+_{Prep}$=number of CD34+ cells in a preparation Accordingly, the preferred embodiment is also a combination in which the stated elements interact to attain a technical overall success, resulting in a synergistic effect which produces an astonishingly efficient and rapid search for adequate preparations. Accordingly, the classification criteria in the sense of the invention can also be described as search criteria. The search can preferably take place automatically, so that the search can take place considerably more rapidly and no errors are made by persons participating in the search. The standardization of the search process and the combination of the classification criteria preferably allows automated mass processing. A particularly preferable aspect of the application is shown as an example in FIG. 2.

The search for a suitable preparation is structured into several stages. The first stage is a "basic search". Following an exclusion principle, the so called "long list" is shown; this preferably comprises all preparations in the order of their rank which match in at least four out of six HLA typings and do not exclude each other in terms of their blood group; that is, there is a resultant match level according to the HLA match between the preparation and the patient. At this time, the clinic can also enter preparations from unregistered UCB-banks into the basic search.

The next level is the "advanced search", wherein it is preferably possible to use a "short list" in two parts. The list preferably comprises possible single transplants (single cord view). These are preparations which are possible single transplants in the correlation of the classification criteria of HLA match, patient weight and number of so called nucleus containing cells (TNC) as well as the number of haematopoietic cells (CD34+). The correlation is based on the following key figures. With an HLA match of six out of six, for instance, the patient requires at least $3.0 \times 10^7$ TNC per kg of patient bodyweight; e.g. if the patient has a bodyweight of 55 kg, the preparation could have a total of at least $1.65 \times 10^9$ nucleus containing cells. With an HLA match of five out of six, for instance, the same patient will require at least $4.0 \times 10^7$ TNC per kg of bodyweight, so that, e.g. with a patient weight of 55 kg, the preparation could contain at least $2.2 \times 10^9$ TNC. Furthermore, with a match of 4 out of 6 HLA types, the preparation might, for instance, have at least $5.0 \times 10^7$ TNC/kg; that is, a total of $2.75 \times 10^9$ TNC. Therefore it is advantageously possible to generate rank lists of the identified preparations, e.g. using two selectable criteria: 1) highest HLA match and following this, highest relative cell count; or 2) highest relative cell count and following this, highest HLA match. If the determined preparations show the same positioning, the further rank of the preparations is specified using the level of the CD34+ cell count.

In the preferred embodiment and particularly with the combination of the criteria which interact synergistically, the best matching umbilical cord blood preparation can be identified out of a given supply and prepared for shipping. The selection of the preparation preferably takes place automatically. It is therefore possible to standardize and accelerate the time-consuming manual selection process which today represents a central weak link in the supply chain of umbilical cord blood preparations.

It is also beneficial that the following classification criteria and/or exclusion criteria are used and individually weighted:
preparations having a CD34+ cell count above 10% of the TNC count,
exclusion of preparations wherein less than 75% of the CD34+ cells survived and/or were activated in a CA (colony assay)
blood group identity
ethnic identity
gender
age of preparation
accreditation standard and/or
ranking of the UCB bank.

The preferred embodiment makes it possible to ensure that optimal preparation quality is guaranteed, allowing a successful transplantation. For this purpose, preparations with a CD34+ cell count higher than 10% of the TNC count are preferably differently weighted. Preparations in whose CA (colony assay) less than 75% of the CD34+ cells survived or were activated are excluded in order to guarantee a high count of haematopoietic stem cells. Further criteria such as blood group identity, ethnic identity and sex can further restrict the selection of the preparation. By determining the age of the preparation, it is also possible to exclude old preparations, which means that advantageously, only preparations which have not exceeded a defined age are used for transplantation, ensuring surprisingly high quality. The accreditation ranking of the UCB-bank can also be used for selection. This makes it possible to exclude banks which e.g. have little experience in the storage or transplantation of cord blood. Combining the classification and/or exclusion criterias allows for a qualitative characterization of the preparations, which reduces rejection of preparations in transplantations and ensures that patients receive the "best" preparation; that is, the preparations which are most compatible for them.

It is preferably possible to specify selection criteria which simplify the search for a suitable preparation and may also make it easier to select a preparation.

It is also possible to use information about the reliability and delivery speed of the UCB-bank which are automatically collected by the system in this process.

These additional classification criteria can be assigned once as part of the clinic policy or newly prioritized in each individual case. The prioritization decides the fine selection in the final ranking of the preparations for the possible solutions.

It is also preferable that the preferred embodiment is used to arrange double or multiple transplantations (multi-cord). Depending on the required cell count, this makes it possible to perform double or multiple transplantations. In other words, if the patient requires more cells than those provided by a matching preparation, another matching preparation can be automatically sought.

It is furthermore preferable that the selection of the multi-cord preparations is performed according to the following classification criteria:

$ML_{P1P2}$=mutual compatibility of 2 preparations:

$$ML_{P1P2} := \begin{cases} 6: HLA_{Prep1} \text{ and } HLA_{Prep2} \text{ match in 6 out of 6 values} \\ \quad \text{and blood group compatibility} \\ 5: HLA_{Prep1} \text{ and } HLA_{Prep2} \text{ match in 5 out of 6 values} \\ \quad \text{and blood group compatibility} \\ 4: HLA_{Prep1} \text{ and } HLA_{Prep2} \text{ match in 4 out of 6 values} \\ \quad \text{and blood group compatibility} \\ \text{Preparation not included: other} \end{cases}$$

$BL_{Multi}$=base list for determining the selection list for multiple preparations $$BL_{Multi} := \left\{ p \in Prep \;\middle|\; \frac{CN_p}{BW_{Pat}} < 1/kg \wedge ML_{Prep} \geq 4 \right\}$$

$SL_{Multi}$=shortlist of preparations to be taken into account for multiple transplants $$SL_{Multi} := \left\{ p1 \in BL_{Multi}, p2 \in BL_{Multi} \;\middle|\; ML_{p1p2} \geq 4 \wedge \frac{CN_{p1} + CN_{p2}}{BW_{Pat}} \geq 1 \right\}$$

The preferred embodiment offers a second part of the short list, containing a multi-cord view with preparations which are matched with each other; that is, they are compatible with each other. Advantageously, the suitability of the various preparations for each other is already defined, which preferably means that no intolerances occur between several preparations which are given to the patient. The shortlist advantageously lists preparations which were thus far not yet considered on their own or in combination and which either reach or even exceed the required cell count. In multi-cord preparations, the (partial) preparation which contains the higher CD34+ cell count should be regarded as preferable (as the "first"). The shortlist shows a temporary budget for each single-cord and multi-cord preparation which calculates the costs of a preparation using standard values according to the status of the preparation.

The search results can be advantageously displayed in a "compare view" with up to four preparations which can be compared to the patient data in a clear overview. The "compare view" compares all data of the unit report to the patient data.

The last stage of the selection process consists of the recommended solutions which are preferably presented to a treating physician in a clear overview. Herein the recommendations preferably comprise single preparations and/or multi-cord preparations. It is the physician's final decision whether and which single-cord or multi-cord preparation he or she chooses.

Folders/files with four sheets can be advantageously generated for each recommended solution. This file is a work and communication instrument for the cooperation of the coordinator with the treating physician or regarding the patient and the clinic management.

This folder may, for instance, be structured as follows:

Page 1 may consist of a work sheet or running list which shows the preparation(s) next to the patient data and the required further steps which can be processed until the transplantation. This primarily involves requests for HR typing, DNA samples and CAs, but also direct contact initiation with the respective UCB-bank, reservations up to the binding order, transport logistics and invoicing until transfer to the clinic administration.

Page 2 of the recommended solution may contain the complete unit report(s).

Page 3 of the recommended solution may be used to document the decision; it summarizes the physician's decision criteria, specifies the final budget and is signed off by the physician. The physician may use this sheet to refer to other recommended solutions which can be used alternatively if the desired recommended solution cannot or can no longer be implemented due to events.

Page 4 may contain a clear overview regarding the preparation, the time progression and the transplantation in general which is available to the physician for the patient discussion or to the patient for information.

Furthermore, recommended solutions can be advantageously documented in the file annex if the first solution cannot be implemented (e.g. due to transport damage or loss of a preparation from the first solution).

The sheets from the recommended solution are available to the clinic for the further progression, such as billing and follow-up of the transplantation, e.g. the patient's medical history, and are passed on to the respective UCB-bank(s) at the appropriate times.

During the entire progression to the patient's follow-up, data from newly registered USB-preparations are preferably sent to the clinic automatically and evaluated regarding the rankings on the long and short lists, as well as with the recommended solutions.

This ensures dynamic improvement of the recommended solutions as well as follow-up treatment of the patient using the most up-to-date data.

In a preferred embodiment, a cell preparation which is suitable for allogeneic transplantation is selected. In allogeneic transplantations, the transplanted tissues do not originate from the recipient himself, but from a donor of the same biological type. In order to avoid a severe and possibly fatal rejection of the foreign tissues, a successful allogeneic transplantation requires that the attributes which are recognized by the immune system must match those of the recipient tissue as closely as possible. Using the specified parameters, the preferred embodiment makes it possible to perform a preferably automated search for a suitable, that is, matching preparation simply and quickly, which surprisingly minimizes the risk of a rejection reaction and nothing stands in the way of a successful transplantation.

In a further preferred embodiment, automatic and complete selection for single-cord or multi-cord transplants takes place. Herein suitable preparations which match each other based on the parameters and do not generate a rejection reaction are recommended to the treating physician and/or to the coordinator. Advantageously, the preparations which match each other and the patient are shown correspondingly in order to considerably simplify and speed up the selection. Accordingly, both selection options can be shown to the treating physician, so that he or she can assess for themselves whether a multi-cord or single-cord transplantation should take place. Surprisingly, automatic selection can avoid errors and present single-cord and/or multi-cord transplants to the treating physician. The presentation is preferably made in a clear overview, simplifying the selection of the preparations by the physician:

It is preferred that the search criteria are adapted to the entered criteria and/or parameters. The current typing status of the UCB-preparation is taken into account in the selection of the suitable preparation. That is, it is e.g. assessed what additional tests etc. are necessary to confirm the preparation as suitable and transplant it. For this purpose, the preferred embodiment utilizes automatically collected statistics regarding the expected costs and required time. This is absolutely necessary, particularly in utilization scenarios in which time is critical, and considerably accelerates the selection process. Fundamentally, the expandability of the data schema of the UCB-preparation(s) and the patient is beneficial in order to allow the adaptation of further search criteria to the future state of the art.

It is furthermore preferred that a matrix is used to show the results obtained with the search criteria and that the results are visually displayed. For this purpose, the preferred embodiment offers a visual orientation regarding the best search results according to the currently selected search parameters. Herein the search results are arranged and visualized in a matrix. The matrix can be dynamically resorted according to the various criteria. The precision of the match according to the preset search criteria is shown in color. In the sense of the invention, the matrix can be described as a heat map in which data of a parameter are shown as colors in a two-dimensional display.

It is furthermore preferred that statistics about expected costs and required time are used for assessing the status of the determination of classification criteria. Advantageously, statistics for the search for a suitable preparation can be used to determine the classification criteria. For instance, the expected costs, the required time, the successful transplantations of a clinic and the tests still to be done can be used here in the selection of a preparation or the classification which a preparation holds. This makes it possible to assess preparations more rapidly and arrange them accordingly. This also enables a search which requires fewer costs and less time.

Consequently automatic and complete recommended solutions can be generated for single-cord or multi-cord transplants. The coordinator and the physician can advantageously concentrate on the suitability of the various well defined and documented recommended solutions. Herein it is preferred that coordination between clinic, transplantation centre and treating physician is performed through preferred embodiment. This makes it possible to ensure that reliable communications take place between clinics—that is, if applicable, the treating physician—and the transplantation centre. The search parameters and the results are presented in a clear overview, significantly simplifying the selection. The parameters, on whose basis the search is performed, are also variable and can be adapted to the patient and/or the sought preparation. This is a major advancement as compared to the current situation, in which coordinators are forced to evaluate possible transplants at a very early time and using different criteria. This leads to unsatisfactory results today and requires a lot of time and personnel effort. Therefore, the preferred embodiment makes it possible to seek and classify one or more matching preparations within a short time.

The invention will be explained in the following text in an exemplary manner, however without being limited to the examples.

The order and search for a suitable preparation may consist of the following steps:

1. New Patient
1.1 Selection of the Physician/Clinic

The patient's physician files a written order to search for a matching umbilical cord blood preparation (UCB-preparation). At the same time, the stem cell transplantation indication is confirmed, which excludes an unjustified search for a UCB-preparation and therefore blocks it from other search processes. The patient is allocated to a physician and a clinic in the system.

1.2. Generation of the Patient File

A patient file—preferably a digital patient file—may be created. The following patient data could be entered into a template with e.g. the following parameters:

| Entry of patient data: e.g. | |
|---|---|
| Name: | H. K. |
| Age: | *1949 |
| Sex: | male |
| Bodyweight | 90 kg |
| Diagnosis: | AML high-risk group |
| HLA parameters: | A*2301, 6801 |
| | B*3501, 4403 |
| | DRB1*1501, 1601 |

The templates or parameters are variable and can preferably be easily expanded with further information.

1.3. Specifying a Search Profile

The search profile is used to define the cord blood parameters which may be suitable, e.g.:

TNC (=Total nucleated Cell Count=number of nucleus-containing cells) Minimum quantity of TNC for the patient: $3 \times 10^7$/kg of the patient. (With a bodyweight of 90 kg, patient H.K. accordingly requires $270 \times 10^7$ TNC in the UCB-preparation.)

Number of CD34+ cells in the UCB-preparation.

Match of the HLA parameters of the patient and the UCB-preparation. The HLA parameters preferably match in 4 out of 6 parameters.

Presence of a precise specification of the UCB-preparation by the cord blood bank (unit report).

Further individual search parameters can be defined. However the search coordinator who performs the search can also pre-set search profiles.

2. Start of the Search
2.1. Single Transplant Search

After entering the patient data into the system and specifying the search parameters, the program performs matching; that is, the characteristic attributes of a preparation are compared to those of the patient. The parameters of the search profile are used as filters. Based on the compatibility, that is, the match of the parameters, a match list is preferably generated for the patient H. K. out of the inventory of all registered UCB-preparations.

2.2. Multi-Transplant Search

If no UCB-preparation with a sufficient cell concentration (TNC) which can be used as the sole source of stem cells for transplantation is found, it is advantageously possible to search for another matching UCB-preparation to provide a sufficient number of cells for successful transplantation. A multi-transplant search can be done for this purpose. The match list is the basis for this further search process. It can be sorted according to the individual specifications of the search coordinator. Herein it is again possible to perform a search for a UCB-preparation. This should preferably match both the patient and the first UCB-preparation in 4 out of 6 HLA parameters. New match lists are generated for this purpose.

3. Generating a Solution

Using the new match lists, several solutions may be shown for a multi-transplant search for the patient H. K. However a minimum quantity of $270 \times 10^7$ cells in the UCB-preparation is nonetheless preferable for the patient H. K.

3.1. Solution Report/Reservation

The various possible solutions are evaluated by the search coordinator. The final selection can be presented to the treating physician in the form of a report. After detailed verification, the latter makes a decision regarding the selection of the individual UCB-preparations.

Orders are submitted to the UCB-bank for each selected UCB-preparation:

The UCB-preparation could be reserved for the patient, wherein this is preferably confirmed by the UCB-bank. Without a reservation, there is no guaranteed availability of the transplant. If a reservation is not possible, another UCB-preparation can be selected. The search process starts again here.

3.2. Verification

A verification can be performed for all UCB-preparations which are defined as solutions. This comprises e.g.:

A DNA sample can be requested for each UCB-preparation. Shipping and receipt is processed and confirmed via the system.

The search coordinator may order high resolution typing from the UCB-bank. The results of this typing process are reported by the UCB-bank via the system.

This system of order submission and confirmation of receipt ensures that all required verifications of the selected UCB-preparations take place very quickly and efficiently. The duration of order processing by the UCB-banks is precisely specified.

3.3 After the transmission of all relevant data for the applicable UCB-preparation, the final selection of the solution(s) is made by the search coordinator in consultation with the treating physician.

3.4 The defined solutions are preferably divided into first and second choices according to the quality of the UCB-preparations. There is preferably a backup solution so that matching UCB-preparations are available at the time of the transplantation.

4. Ordering UCB-Preparations
4.1. The UCB-preparations are ordered as soon as the treating physician has specified the transplantation date. The UCB-bank is informed about this date at the earliest possible time so that appropriate preparations can be made. This particularly comprises readying a nitrogen container for transporting the UCB-preparations. The actual transport is organized by the UCB-bank, since they have the information about when the transplant is ready for pick-up. If the UCB-bank determines that transport is not possible, e.g. because the UCB-preparation is damaged, the backup solution can be used.

4.2. When the UCB-preparation has been received at the transplantation centre, the flawless condition of the nitrogen container in which the preparation was transported and of the UCB-preparation is verified, and confirmed to the UCB-bank. For instance, interruptions in the cooling chain may have dramatic effects on the viability of the cells in the UCB-preparation.

4.3. Receipt Verification of the UCB-Preparations

The laboratory of the transplantation clinic can again test the HLA parameters, determine the cell count after thawing the UCB-preparation, and test the vitality of the cells. After this receipt control, the UCB-preparation is available to the patient.

5. Transplantation

It is beneficial if the transplantation is performed immediately after the receipt control, since the cells of the UCB-preparation should be administered immediately.

The processes from 4.1 to 5. can be performed for each individual UCB-preparation. Particularly in multi-transplant requests which come from different UCB-banks, careful coordination of the order is required to ensure simultaneous arrival of the various UCB-preparations at the transplantation centre.

6. Follow-up

After transplantation, the patient's initial clinical data (e.g. conditioning protocol, underlying illness, previous chemotherapy protocols) can be collected. This can be immediately followed by recording the progression of the transplantation, e.g.:

Duration of engraftment (time taken by the transplant to grow into place).

Duration until the transplant is functioning.

Clinical problems due to a possible rejection reaction.

These detailed clinical data are preferably also reported to the UCB-banks, since such information is important for quality assurance. Follow-up after a transplantation takes place at regular intervals.

The greatest benefit of cryopreserved UCB-preparations as compared to preparations from donors (bone marrow, peripheral blood) lies in its immediate ready-to-use availability. In practice, this immediate availability can only become effective with a system as described above.

Figure 2:
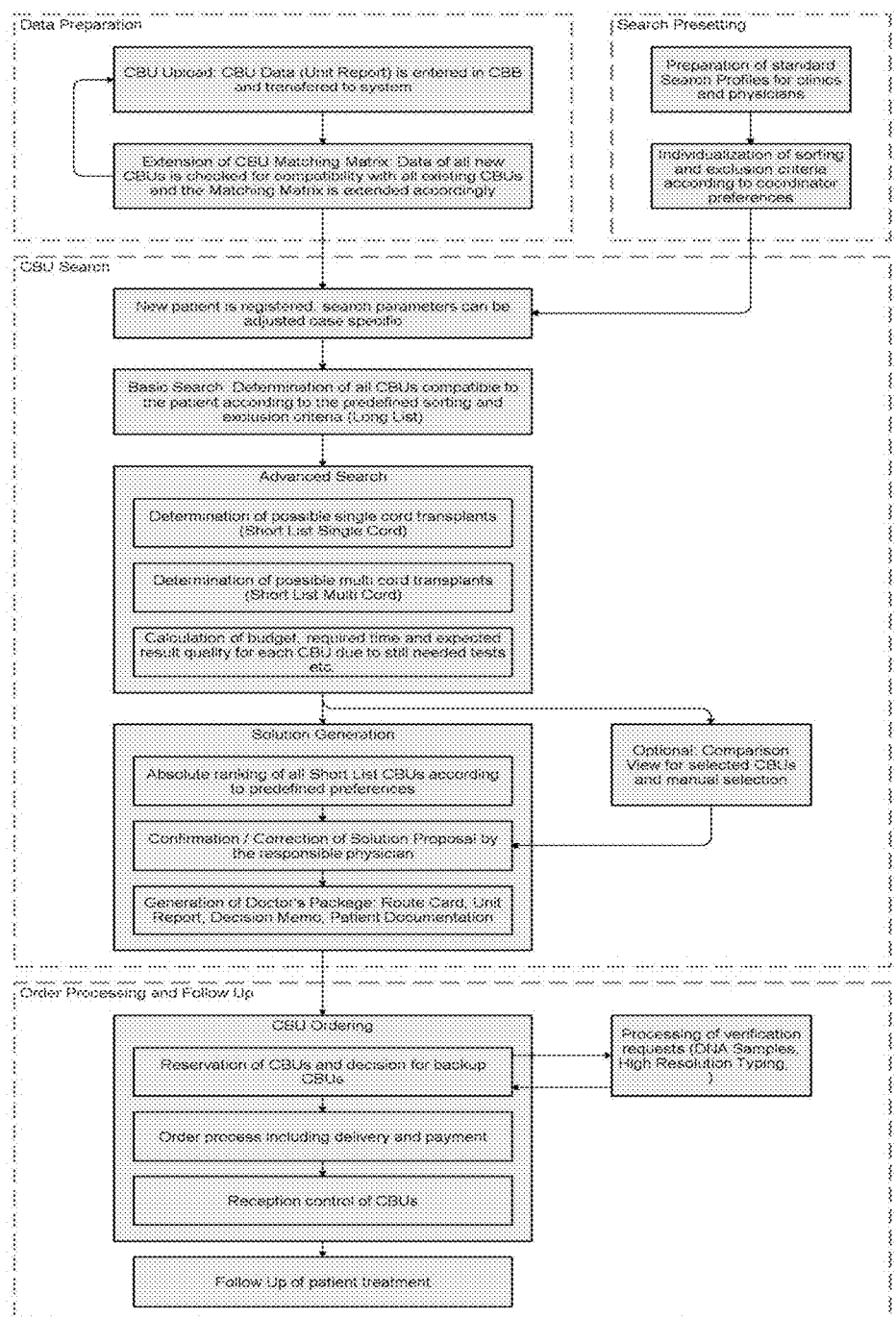
Figure 3:
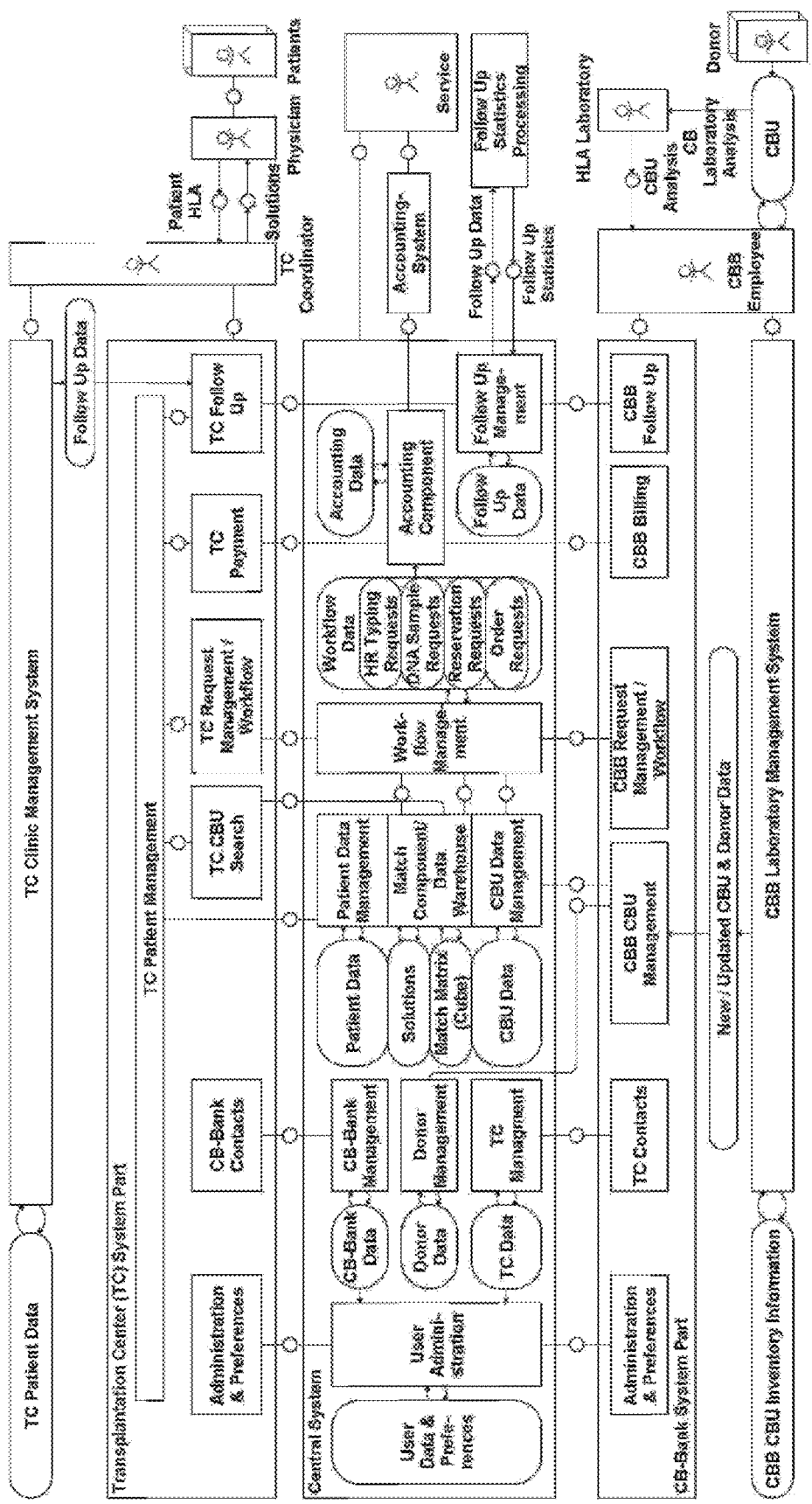

The invention is always explained in an exemplary manner through the use of figures, without being limited to the examples. The following show:

FIG. 1 The base data model
FIG. 2 The process progression
FIG. 3 The system architecture FIG. 1 shows an exemplary depiction of a preferred embodiment of the base data model. In initial contact, the data of a person can be recorded, such as the name, address and other contact information. This may, for instance, be a UCB-donor, wherein further data are also entered into the database (comprising the birth clinic and the medical history of the mother, father and/or child). It is preferably also possible to record and save data of the UCB-bank. Beneficial data comprise the processing quality and a specific bank ID. The data of the UCB-preparations preferably comprise the HLA type, TNC number or viral status. Using this information, a preparation can be precisely characterized, wherein additional information about the preparation is provided by further tests (comprehensive high resolution HLA typing or colony assays). The preparation is examined in the tests, and quality is simple to assess. The data of the preparation are advantageously compared to the data of a transplantation patient; for instance, the blood group and urgency can be compared. Based on the comparison, the preparation can be advantageously reserved for the patient by the transplantation clinic. This may, for instance, be done by a coordinator or a treating physician at the hospital. Clinic data can preferably be recorded and saved in a preferred database. Herein the data can comprise a clinic ID or accreditation type.

FIG. 2 shows an exemplary depiction of the process progression. During data processing, new UCB-preparations in the UCB-bank can be recorded and entered into the preferred system. The newly recorded preparations can preferably be compared to the UCB-preparations which are already in the system for compatibility. This may, for instance, take place advantageously via a compatibility matrix. When a UCB-preparation is sought, the standard search profiles for clinics and physicians can be used, wherein it is preferably also possible to individualize the order and exclusion criteria according to the coordination preference. The search for a UCB-preparation which is suitable for a transplantation patient can also be adapted specifically for the case. A so called basic search can take place, in which all UCB-preparations which are compatible with the patient according to the pre-set classification and/or exclusion criteria are preferably sought (long list). It may also be beneficial to perform a so called advanced search which determines the possible single transplants (single-cord) and/or multiple transplants (multi-cord). The required budget, the required time, as well as the result quality for each transplant based on the tests still to be done could also be displayed advantageously. Herein the found preparations can be compared in a comparison view, wherein it is also possible to compare individual preparations with each other. It is preferably possible to generate a solution which sorts the shortlist preparations according to the specified references. In this manner, the treating physician can be presented with a clear overview of the preparations, wherein the generated recommended solution can be advantageously confirmed or corrected by the physician. The solution which is generated in this manner can be added to the transplantation patient's patient file, including the running lists, unit report, decision basis and patient documentation. In this manner, all relevant information for UCB-transplantations can be advantageously stored in one file. When the transplantation clinic or the treating physician have selected one or more UCB-preparations, the preparation(s) can be ordered from the UCB-bank. It is advantageously possible to select the preparations which were found with the search for a patient or clinic, wherein it is preferably possible to define backup preparations if the selected preparations are not available. Additional verifications (comprising DNA samples and high resolution typing) can also ensure the quality and compatibility of the preparations. Following selection, the samples can be ordered and delivered. The preparations are preferably subjected to receipt controls by the clinic. Following successful transplantation, it is advantageously possible to perform a patient follow-up.

FIG. 3 shows an exemplary depiction of the preferred system architecture.

The depiction shows a schematic structure of a preferred data processing system part. The preferred embodiment of the system can be structured into three fields—the central system, the TC (transplantation centre) system part and the umbilical cord blood bank (UCB-bank) subsystem. The system is preferably usable via the internet and the intranet. It is shown that UCB-preparations can be supplied from donors and analyzed by an HLA laboratory. The preparations can preferably be physically processed by the UCB-bank and stored, wherein the data collected about the UCB-preparation can preferably be managed with the UCB-bank in a laboratory management system. Information about selected UCB-preparations can, for instance, be entered into the central system decentrally and incrementally as data sets.

The preferred system preferably provides the umbilical cord blood bank with the option of administration, viewing contact information of the transplantation centre (TC) contact persons, management of the entered UCB-preparations, comfortable processing of inquiries and work flow management, administration of complete billing of UCB-preparation deliveries and services, as well as administration of follow-up information. FIG. 3 furthermore shows that a physician can determine HLA parameters of the patient and e.g. pass them on to the TC coordinator for the search for UCB-preparations along with further information. The coordinator may, for instance, perform a system supported search and provide recommended solutions, and preferably UCB-preparations, for transplantations. The transplantation centre or the clinic can administer patient data in a separate management system. It is preferably possible to pass follow-up information on to the central system from this system following the transplantation. The preferred system preferably provides the transplantation centre with the option of administration, viewing contact information of the UCB-bank contact persons, searches for UCB-preparations, comfortable ordering and management of inquiries and work flow management, administration of complete billing of UCB-preparation deliveries and services, as well as administration of follow-up information. The central system can preferably enable secure access to the data which are stored in the encoded form to preserve data security (e.g. in a database system). The user data and their settings can preferably be stored centrally, so that they are available from session to session. The administration of the central component (comprising set-up of new users, clinics and UCB-banks) may be performed e.g. by service personnel.

Information which is uploaded by the UCB-bank can be administered in donor management and central UCB-preparation management. The UCB-data can be presorted by classification criteria (which are e.g. exchangeable in a modular manner) (e.g. through a data warehouse cube) in order to advantageously guarantee a rapid, efficient search even in complex multiple transplantations. The matching component can preferably utilize modular differing matching algorithms to automatically or partly automatically generate suitable solutions. All processes and interactions between the involved parties can be controlled through the work flow component. Furthermore all transactions and services can be recorded and evaluated by the billing component. Processed billing information can preferably be transferred to a bookkeeping system, e.g. for invoicing. The follow-up information can be centrally administered and passed on to an external central location which can, for instance, generate follow-up statistics and regularly transfer these again.

The invention claimed is:

1. A system for the allocation and selection of umbilical cord blood preparations, for transplantations, therapies and/or research purposes, wherein
the system comprises umbilical cord preparations and data processing systems which are configured to:
process data,
preset search criteria to search the data of registered cell preparations,
search the data of incoming patients,
compare the incoming patient data to the data of registered cell preparations and
process and track an order, wherein the umbilical cord blood preparations are arranged and selected according to HLA match, patient weight, number of nucleated cells (TNC) and number of hematopoietic cells (CD34+),
wherein the data processing systems are configured to execute a patient search that comprises determining patient-compatible preparations in accordance with one or more of the following:
name and identification of clinic or transplantation center,
names of coordinator and attending physician, including contact data,
status of clinic with regard to international certifications,
average number of UCB transplantations in the inquiring clinic during the last three years,
name of patient, insurance number and other accounting information,
patient's medical history,
indication and therapy proposal of attending physician,
urgency according to defined classification,
HLA type of patient,
blood group of patient,
weight of patient,
ethnic group of patient,
sex of patient,
age of patient,
known allelic characteristics of patient and/or data of DNA typing, and/or
first treatment or re-treatment,
wherein
the data processing systems are configured to produce short list(s) of potential umbilical cord preparations using the following settings:

$$ML_{Prep} := \begin{cases} 6: HLA_{Prep} \text{ and } HLA_{Pat} \text{ match in 6 out of 6 typing} \\ \quad \text{values and blood group compatibility} \\ 5: HLA_{Prep} \text{ and } HLA_{Pat} \text{ match in 5 out of 6 typing} \\ \quad \text{values and blood group compatibility} \\ 4: HLA_{Prep} \text{ and } HLA_{Pat} \text{ match in 4 out of 6 typing} \\ \quad \text{values and blood group compatibility} \\ \text{Preparation not included: other} \end{cases}$$

wherein $MLp_{Prep}$=match level in accordance with HLA compatibility between preparation and patient, $$CF_{Prep} := \begin{cases} 3 \times 10^7: ML_{Prep} = 6 \\ 4 \times 10^7: ML_{Prep} = 5 \\ 5 \times 10^7: ML_{Prep} = 4 \end{cases}$$

wherein $CF_{Prep}$=cell factor defining the required number of cells per kg of patient weight at corresponding match level, $$CN_{Prep} := \frac{TNC_{Prep}}{CF_{Prep}}$$

wherein $CN_{Prep}$=classification number of a preparation allowing arrangement of preparations in accordance with TNC and match level, and wherein
the short list(s) of preparations to be considered for single transplants are produced using the following setting:

$$SL_{Single} := \left\{ p \in Prep \,\middle|\, \frac{CN_p}{BW_{Pat}} \geq 1/kg \wedge ML_{Prep} \geq 4 \right\}$$

wherein $SL_{Single}$=short list of preparations to be considered for single transplants
and wherein the classifications of preparations in the short list are made according to the following criteria:
Classification 1=initial ranking according to match level, followed by classification number, followed by CD34+

$$\text{Classification 1 } (SL) := \left\{ p1 \in SL, \; p2 \in SL \,\middle|\, \begin{array}{l} \text{either } ML_{p1} > ML_{p2} \\ \text{or } ML_{p1} = ML_{p2} \wedge CN_{p1} > CN_{p2} \\ \text{or } ML_{p1} = ML_{p2} \wedge CN_{p1} = CN_{p2} \wedge CD34_{p1} \geq CD34_{p2} \end{array} \right.$$

Classification 2=initial ranking according to classification number, followed by match level, followed by CD34+

$$\text{Classification 2 } (SL) := \left\{ p1 \in SL, \; p2 \in SL \,\middle|\, \begin{array}{l} \text{either } CN_{p1} > CN_{p2} \\ \text{or } CN_{p1} = CN_{p2} \wedge ML_{p1} > ML_{p2} \\ \text{or } CN_{p1} = CN_{p2} \wedge ML_{p1} = ML_{p2} \wedge CD34^+_{p1} \geq CD34^+_{p2} \end{array} \right.$$

wherein
Prep=umbilical cord blood preparation
Pat=patient
$HLA_{Pat}$=HLA values of patient
$HLA_{Prep}$=HLA values of preparation
$TNC_{Prep}$=number of nucleated cells of preparation
$BW_{Pat}$=body weight of patient in kq
$CD34+_{Prep}$=number of CD34+ cells of a preparation
p1, p2=preparation 1 selected, preparation 2 selected.

2. The system according to claim 1,
wherein the data processing systems are configured to acquire data regarding umbilical cord blood preparations with a data set during data processing, which data set comprises the following parameters:
name and identification of the UCB storage bank (UCB bank),
status of the UCB storage bank with regard to international certifications, preferably Fact,
process reliability of the UCB bank according to classification,
contact in the respective bank, including contact data,
identification number of preparation,
medical history of mother, child and family according to anamnesis form of the maternity clinic,
ethnic group of mother, father and/or child,
sex of child,
date of initial storage of preparation,
details of preparation processing,
blood group of preparation,
HLA type of preparation,
cell count (TNC) of preparation,
cell count (CD34+) of preparation,
viral status of preparation, and/or
allelic characteristics of preparation.

3. The system according to claim 1,
wherein the following further classification and/or exclusion criteria are implemented:
preparations having a CD34+ cell count above 10% of the TNC count,
exclusion of preparations wherein less than 75% of the CD34+ cells survived and/or were activated in a CA (colony assay),
blood group identity,
ethnic identity,
sex,
age of preparation,
accreditation standard and/or
ranking of the UCB bank.

4. The system according to claim 1,
wherein data processing systems are configured to allocate double or multiple transplantations (multi-cord).

5. The system according to claim 4,
wherein data processing systems are configured to perform the selection of multi-cord preparations according to the following classification criteria:

$$ML_{P1P2} := \left\{ \begin{array}{l} 6\text{: } HLA_{Prep1} \text{ and } HLA_{Prep2} \text{ match in 6 out of 6 typing} \\ \quad \text{values and blood group compatibility} \\ 5\text{: } HLA_{Prep1} \text{ and } HLA_{Prep2} \text{ match in 5 out of 6 typing} \\ \quad \text{values and blood group compatibility} \\ 4\text{: } HLA_{Prep1} \text{ and } HLA_{Prep2} \text{ match in 4 out of 6 typing} \\ \quad \text{values and blood group compatibility} \\ \text{Preparation not included: other} \end{array} \right\}$$

wherein $ML_{P1P2}$=mutual compatibility of 2 preparations, $$BL_{Multi} := \left\{ p \in Prep \,\middle|\, \frac{CN_p}{BW_{Pat}} < 1/kg \wedge ML_{Prep} \geq 4 \right\}$$

wherein $BL_{Multi}$=basic list to determine the selection list for multiple preparations and wherein the data processing systems are configured to produce short list(s) of potential umbilical cord preparation using the following settings:

$$SL_{Multi} := \left\{ p1 \in BL_{Multi}, \, p2 \in BL_{Multi} \,\middle|\, ML_{p1p2} \geq 4 \wedge \frac{CN_{p1} + CN_{p2}}{BW_{Pat}} \geq 1 \right\}$$

wherein $SL_{Multi}$=short list of preparations to be included in multiple transplants, and wherein
P1=preparation 1 selected,
P2=preparation 2 selected, and
Multi=multiple transplants.

* * * * *